United States Patent
June et al.

(10) Patent No.: US 9,783,591 B2
(45) Date of Patent: Oct. 10, 2017

(54) USE OF THE CD2 SIGNALING DOMAIN IN SECOND-GENERATION CHIMERIC ANTIGEN RECEPTORS

(71) Applicant: The Trustees of the University of Pennsylvania, Philadelphia, PA (US)

(72) Inventors: Carl H. June, Merion Station, PA (US); John Scholler, Narberth, PA (US); Avery D. Posey, Jr., Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 223 days.

(21) Appl. No.: 14/375,999

(22) PCT Filed: Feb. 22, 2013

(86) PCT No.: PCT/US2013/027361
§ 371 (c)(1),
(2) Date: Jul. 31, 2014

(87) PCT Pub. No.: WO2013/126729
PCT Pub. Date: Aug. 29, 2013

(65) Prior Publication Data
US 2014/0370045 A1  Dec. 18, 2014

Related U.S. Application Data

(60) Provisional application No. 61/601,907, filed on Feb. 22, 2012.

(51) Int. Cl.
| | | |
|---|---|---|
| C07K 14/705 | (2006.01) | |
| C07K 14/725 | (2006.01) | |
| C12N 15/85 | (2006.01) | |
| C07K 16/28 | (2006.01) | |
| C07K 16/30 | (2006.01) | |

(52) U.S. Cl.
CPC ........ *C07K 14/7051* (2013.01); *C07K 14/705* (2013.01); *C07K 14/70507* (2013.01); *C07K 16/2803* (2013.01); *C07K 16/30* (2013.01); *C12N 15/85* (2013.01); *C07K 2319/00* (2013.01); *C07K 2319/02* (2013.01)

(58) Field of Classification Search
None
See application file for complete search history.

(56) References Cited

U.S. PATENT DOCUMENTS

| | | | |
|---|---|---|---|
| 5,199,942 A | 4/1993 | Gillis | |
| 5,858,358 A | 1/1999 | June et al. | |
| 5,883,223 A | 3/1999 | Gray | |
| 6,120,766 A | 9/2000 | Hale et al. | |
| 6,233,482 B1 | 5/2001 | Hoffmann et al. | |
| 6,241,701 B1 | 6/2001 | Hoffmann | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 2003/0077249 A1* | 4/2003 | Bebbington ......... | C07K 14/705 424/93.2 |
| 2004/0043401 A1 | 3/2004 | Sadelain et al. | |
| 2004/0092907 A1 | 5/2004 | Mathiesen et al. | |
| 2004/0101519 A1 | 5/2004 | June et al. | |
| 2005/0113564 A1 | 5/2005 | Campana et al. | |
| 2006/0034810 A1 | 2/2006 | Riley et al. | |
| 2006/0121005 A1 | 6/2006 | Berenson et al. | |
| 2007/0128708 A1 | 6/2007 | Gamelin | |
| 2008/0075744 A1 | 3/2008 | Hiserodt et al. | |
| 2011/0223129 A1 | 9/2011 | Jensen | |
| 2015/0017141 A1* | 1/2015 | June .................... | C07K 14/705 424/93.21 |

FOREIGN PATENT DOCUMENTS

| | | |
|---|---|---|
| WO | WO96/23814 | 8/1996 |
| WO | WO0129058 | 4/2001 |
| WO | WO01/96584 | 12/2001 |
| WO | WO 2005/044996 | 5/2005 |
| WO | WO 2010/025177 | 3/2010 |

OTHER PUBLICATIONS

Bachmann et al., "T cell responses are governed by avidity and co-stimulatory thresholds." 1996, Eur J Immunol, 26(9):2017-22.
Berge et al., "Selective Expansion of a Peripheral Blood CD8+ Memory T Cell Subset Expressing Both Granzyme B and L-Selectin During Primary Viral Infection in Renal Allograft Recipients." 1998, Transplant Proc. 30(8):3975-3977.
Bierer et al., "Cyclosporin A and FK506: Molecular mechanisms of immunosuppression and probes for transplantation biology." 1993, Curr. Opin. Immun. 5:763-773.
Borthwick et al., "Factors that influence activated CD8+ T-cell apoptosis in patients with acute herpesvirus infections: loss of costimulatory molecules CD28, CD5 and CD6 but relative maintenance of Bax and Bcl-X expression." 1996, Immunology, (4):508-15.

(Continued)

*Primary Examiner* — Ilia Ouspenski
(74) *Attorney, Agent, or Firm* — Saul Ewing LLP; Kathryn Doyle

(57) ABSTRACT

The present invention provides compositions and methods for treating cancer in a human. The invention includes relates to administering a genetically modified T cell expressing a CAR having an antigen binding domain, a transmembrane domain, a CD2 signaling domain, and a CD3 zeta signaling domain. The invention also includes incorporating CD2 into the CAR to alter the cytokine production of CAR-T cells in both negative and positive directions.

2 Claims, 8 Drawing Sheets

(56) References Cited

OTHER PUBLICATIONS

Brentjens et al, "Treatment of Chronic Lymphocytic Leukemia With Genetically Targeted Autologous T Cells: Case Report of an Unforeseen Adverse Event in a Phase I Clinical Trial." 2010, Mol Ther, 8(4):666-8.
Cougot, et al., "'Cap-tabolism'." 2001, Trends in Biochem. Sci., 29:436-444 (Abstract).
Elango, et al., "Optimized transfection of mRNA transcribed from a d(A/T)100 tail-containing vector." 2005, Biochim. Biophys. Res. Commun., 330:958-966 (Abstract).
Garland et al., "The use of Teflon cell culture bags to expand functionally active CD8+ cytotoxic T lymphocytes." 1999, J. Immunol Meth. 227(1-2):53-63.
Haanen et al., "Selective Expansion of Cross-reactive CD8+ Memory T Cells by Viral Variants." 1999, J. Exp. Med. 190(9):13191328.
Henderson et al., "Comparison of the effects of FK-506, cyclosporin A and rapamycin on IL-2 production." 1991, Immun. 73:316-321.
International Search Report for PCT/US2013/027361 dated May 6, 2013.
Liu et al., "Calcineurin is a Common Target of Cyclophilin-Cyclosporin A and FKBP-FK506 Complexes" Cell 66:807-815, 1991.
Morgan et al, "Case Report of a Serious Adverse Event Following the Administration of T Cells Transduced With a Chimeric Antigen Receptor Recognizing ERBB2." 2010, Mol Ther, 18(4):843-51.
Mumtaz et al., "Design of liposomes for circumventing the reticuloendothelial cells." 1991 Glycobiology 5: 505-10.
Nacheva and Berzal-Herranz, "Preventing nondesired RNA-primed RNA extension catalyzed by T7 RNA polymerase." 2003, Eur. J. Biochem., 270:1458-65.
Nishikawa, et al. "Nonviral vectors in the new millennium: Delivery barriers in gene transfer." 2001, Hum Gene Ther., 12(8):861-70 (Abstract).
Pillmer "Modulation of Regulatory T Cells by Cytokines." 2007, Dissertation presented to University of Pittsburgh School of Medicine.
Porter et al., "Chimeric Antigen Receptor-Modified T Cels in Chronic Lymphoid Leukemia." 2011, N Engl J Med, 365:725-33.
Ren-Heidenreich et al., "Comparison of the TCR zeta-chain with the FcR gamma-chain in chimeric TCR constructs for T cell activation and apoptosis." 2001, Curr Gene Ther, 1(3):253-5 (Abstract).
Ren-Heidenreich et al., "Life or death of T cells with antigen-specific receptors—using T cells for cancer adoptive immunotherapy/gene therapy." 2002, Cancer Immunol Immunother, 2002:417-23 (Abstract).
Rosenberg et al., "Use of Tumor-Inflitrating Lymphocytes and Interleukin-2 in the Immunotherapy of Patients with Metastatic Melanoma." 1988, New Eng. J. of Med. 319:1676.
Schenborn and Mierendorf, "A novel transcription property of SP6 and T7 RNA polymerases: Dependence on template structure." 1985, Nuc Acids Res., 13:6223-36.
Stepinski, et al., "Synthesis and propertys of mRNAs containing the novel "anti-reverse" cap analogs 7-methyl(3'-O-methyl) GpppG and 7-methyl(3'-deoxy)GpppG." 2001, RNA, 7:1468-95.
Ui-Tei et al., "Sensitive assay of RNA interference in *Drosophila* and Chinese hamster cultured cells using firefly luciferase gene as target." 2000 FEBS Letters 479: 79-82.
Viola et al., "T cell activation determined by T cell receptor number and tunable thresholds." 1996, Science. 273(5271):104-6 (Abstract).
Cheadle et al., "Ligation of the CD2 co-stimulatory receptor enhances IL-2 production from first-generation chimeric antigen receptor T cells." Gene Therapy, 19(11):1114-1120, 2011.
Singapore Patent Application No. 11201404284S—Written Opinion dated Apr. 22, 2016.
Japanese Patent Application No. 201380010713X—First Office Action dated Apr. 7, 2016.
Australian Patent Application No. 2013222284—First Examination Report dated Sep. 23, 2016.
Eurasian Patent Application No. 201491573—Office Action issued Mar. 24, 2016.
European Patent Application No. 137551899.9—Extended European Search Report dated Sep. 1, 2015.
Singapore Patent Application No. 11201404284S—Search Report dated Jun. 10, 2015.
Singapore Patent Application No. 11201404284S—Written Opinion dated Aug. 28, 2015.
Howard et al., "The CD3 zeta cytoplasmic domain mediates CD2-induced T cell activation." 1992, J Exp Med 176(1):139-145.
Moingeon et al., "CD3 zeta dependence of the CD2 pathway of activation in T lymphocytes and natural killer cells." 1992, Proc Natl Acad Sci USA 89(4):1492-1496.

* cited by examiner

CD19: CD2zeta CAR

ATGGCCTTACCAGTGACCGCCTTGCTCCTGCCGCTGGCCTTGCTGCTCCACGCCGCCAGG
CCGGACATCCAGATGACACAGACTACATCCTCCCTGTCTGCCTCTCTGGGAGACAGAGTC
ACCATCAGTTGCAGGGCAAGTCAGGACATTAGTAAATATTTAAATTGGTATCAGCAGAA
ACCAGATGGAACTGTTAAACTCCTGATCTACCATACATCAAGATTACACTCAGGAGTCCC
ATCAAGGTTCAGTGGCAGTGGGTCTGGAACAGATTATTCTCTCACCATTAGCAACCTGG
AGCAAGAAGATATTGCCACTTACTTTTGCCAACAGGGTAATACGCTTCCGTACACGTTCG
GAGGGGGGACCAAGCTGGAGATCACAGGTGGCGGTGGCTCGGGCGGTGGTGGGTCGG
GTGGCGGCGGATCTGAGGTGAAACTGCAGGAGTCAGGACCTGGCCTGGTGGCGCCCTC
ACAGAGCCTGTCCGTCACATGCACTGTCTCAGGGGTCTCATTACCCGACTATGGTGTAAG
CTGGATTCGCCAGCCTCCACGAAAGGGTCTGGAGTGGCTGGGAGTAATATGGGGTAGT
GAAACCACATACTATAATTCAGCTCTCAAATCCAGACTGACCATCATCAAGGACAACTCC
AAGAGCCAAGTTTTCTTAAAAATGAACAGTCTGCAAACTGATGACACAGCCATTTACTAC
TGTGCCAAACATTATTACTACGGTGGTAGCTATGCTATGGACTACTGGGGCCAAGGAAC
CTCAGTCACCGTCTCCTCACCACGACGCCAGCGCCGCGACCACCAACACCGGCGCCCACC
ATCGCGTCGCGGCCCCTGTCCCTGCGCCCAGAGGCGTGCCGGCCAGCGGCGGGGGGCG
CAGTGCACACGAGGGGGCTGGACTTCGCCTGTGATATCTACATCTGGGCGCCCTTGGCC
GGGACTTGTGGGGTCCTTCTCCTGTCACTGGTTATCACCCTTTACTGCACCAAAAGGAAA
AAACAGAGGAGTCGGAGAAATGATGAGGAGCTGGAGACAAGAGCCCACAGAGTAGCT
ACTGAAGAAGGGGCCGGAAGCCCCACCAAATTCCAGCTTCAACCCCTCAGAATCCAGC
AACTTCCCAACATCCTCCTCCACCACCTGGTCATCGTTCCCAGGCACCTAGTCATCGTCCC
CCGCCTCCTGGACACCGTGTTCAGCACCAGCCTCAGAAGAGGCCTCCTGCTCCGTCGGG
CACACAAGTTCACCAGCAGAAAGGCCCGCCCCTCCCCAGACCTCGAGTTCAGCCAAAAC
CTCCCCATGGGGCAGCAGAAAACTCATTGTCCCCTTCCTCTAATATCGATAGAGTGAAGT
TCAGCAGGAGCGCAGACGCCCCCGCGTACCAGCAGGGCCAGAACCAGCTCTATAACGA
GCTCAATCTAGGACGAAGAGAGGAGTACGATGTTTTGGACAAGAGACGTGGCCGGGAC
CCTGAGATGGGGGGAAAGCCGAGAAGGAAGAACCCTCAGGAAGGCCTGTACAATGAA
CTGCAGAAAGATAAGATGGCGGAGGCCTACAGTGAGATTGGGATGAAAGGCGAGCGC
CGGAGGGGCAAGGGGCACGATGGCCTTTACCAGGGTCTCAGTACAGCCACCAAGGACA
CCTACGACGCCCTTCACATGCAGGCCCTGCCCCCTCGCTAA

Figure 1

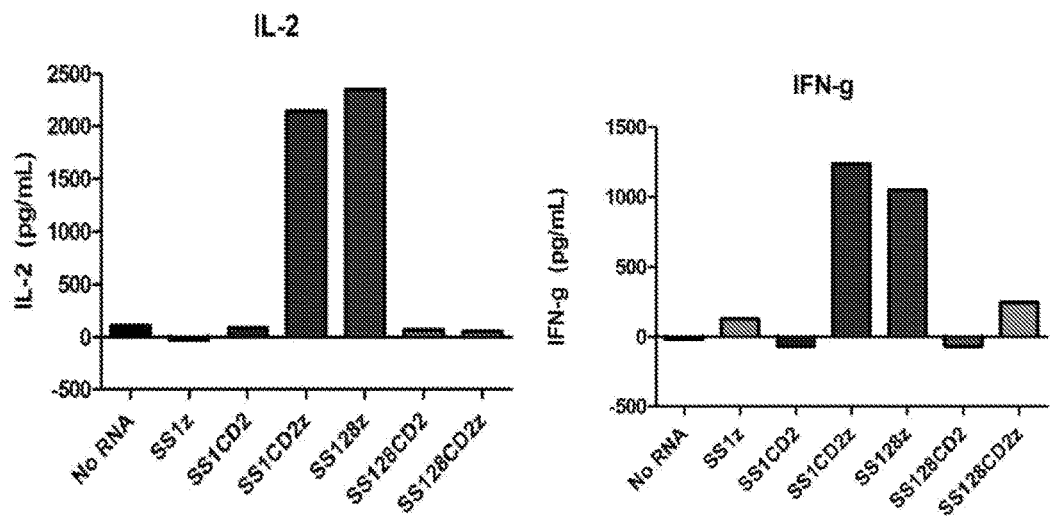
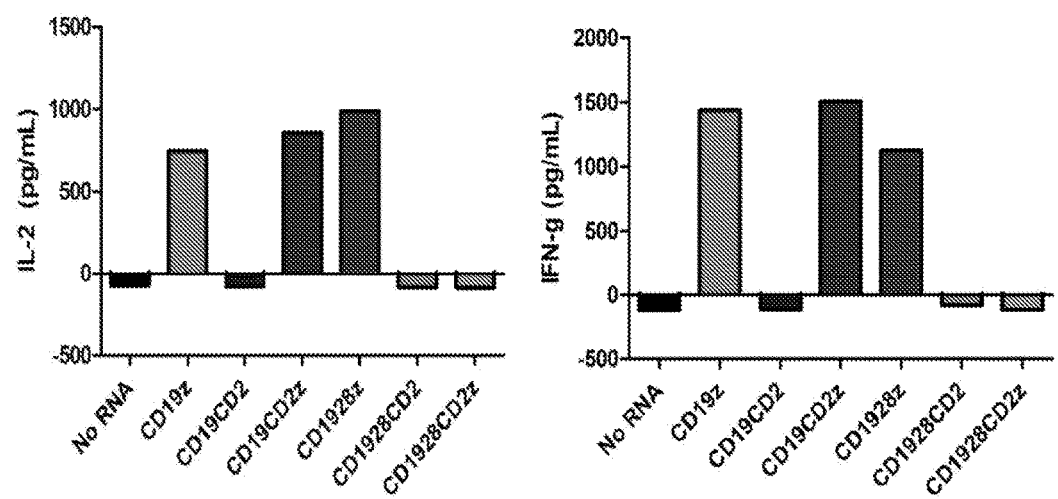
Figure 3

USE OF THE CD2 SIGNALING DOMAIN IN SECOND-GENERATION CHIMERIC ANTIGEN RECEPTORS

CROSS-REFERENCE TO RELATED APPLICATION

This application is the U.S. national phase application filed under 35 U.S.C. §371 claiming benefit to International Patent Application No. PCT/US2013/027361 filed on Feb. 22, 2013, which is entitled to priority under 35 U.S.C. §119(e) to U.S. Provisional Application No. 61/601,907, filed Feb. 22, 2012, each of which is hereby incorporated by reference in its entirety.

STATEMENT REGARDING FEDERALLY SPONSORED RESEARCH OR DEVELOPMENT

This invention was made with government support under grant CA120409 awarded by the National Cancer Institute. The government has certain rights in the invention.

BACKGROUND OF THE INVENTION

T lymphocytes modified with chimeric-antigen receptors (CARs) bearing the CD3-zeta signaling domain exhibit moderate levels of target tumor cytolysis and low amounts of cytokine production. The incorporation of costimulatory signaling domains, usually that of CD28 or 4-1BB, into second-generation CARs significantly increases target cell killing and cytokine production. It has been shown that ligation of the natural CD2 molecule resulted in quantitative and qualitative differences compared to TCR-induced calcium signal transduction. Recent reports demonstrated that ligation of the endogenous CD2 receptor significantly increases IL-2 produced from first-generation CAR-T cells.

Current data indicates that CAR T cells need to engraft and survive in patients who have clinically beneficial tumor responses (Porter et al., 2011, N Engl J Med, 365:725-33). However, activation-induced T cell death can occur when the threshold for too much signal transduction is reached (Viola et al., 1996, Science. 273(5271):104-6; Ren-Heidenreich et al., 2002, Cancer Immunol Immunother, 2002:417-23; Bachmann et al., 1996, Eur J Immunol, 26(9):2017-22; Ren-Heidenreich et al., 2001, Curr Gene Ther, 1(3):253-5; Borthwick et al., 1996, Immunology, (4):508-15).

Thus, there is an urgent need in the art for compositions of CARs that regulate T cell responses to enhance CAR T cell survival and provide a beneficial environment for anti-tumor activity. The present invention addresses this need.

SUMMARY OF THE INVENTION

The invention provides an isolated nucleic acid sequence encoding a chimeric antigen receptor (CAR), wherein the CAR comprises an antigen binding domain, a transmembrane domain, a costimulatory signaling region, and a CD3 zeta signaling domain, wherein the costimulatory signaling region comprises the CD2 signaling domain.

In one embodiment, the CAR comprises the nucleic acid sequence of SEQ ID NO: 1.

In one embodiment, the antigen binding domain is an antibody or an antigen-binding fragment thereof. In one embodiment the antigen-binding fragment is a Fab or a scFv. In one embodiment, the antigen binding domain binds to a tumor antigen. In one embodiment the tumor antigen is associated with a hematologic malignancy. In one embodiment, the tumor antigen is associated with a solid tumor. In one embodiment, tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1 TCR, MAGE A3 TCR, and any combination thereof.

In one embodiment, the costimulatory signaling region further comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD7, LIGHT, NKG2C, B7-H3, a ligand that specifically binds with CD83, and any combination thereof.

The invention also provides an isolated chimeric antigen receptor (CAR) comprising an antigen binding domain, a transmembrane domain, a costimulatory signaling region, and a CD3 zeta signaling domain, wherein the costimulatory signaling region comprises the CD2 signaling domain.

The invention also provides a vector comprising a nucleic acid sequence encoding a chimeric antigen receptor (CAR), wherein the CAR comprises an antigen binding domain, a transmembrane domain, a costimulatory signaling region, and a CD3 zeta signaling domain, wherein the costimulatory signaling region comprises the CD2 signaling domain.

The invention also provides a cell comprising a nucleic acid sequence encoding a chimeric antigen receptor (CAR), the CAR comprising an antigen binding domain, a transmembrane domain, a costimulatory signaling region, and a CD3 zeta signaling domain, wherein the costimulatory signaling domain comprises the CD2 signaling domain.

In one embodiment, the cell is selected from the group consisting of a T cell, a Natural Killer (NK) cell, a cytotoxic T lymphocyte (CTL), and a regulatory T cell.

In one embodiment, the cell exhibits an anti-tumor immunity when the antigen binding domain binds to its corresponding antigen.

The invention also provides a method for stimulating a T cell-mediated immune response to a target cell population or tissue in a mammal, the method comprising administering to a mammal an effective amount of a cell genetically modified to express a CAR, wherein the CAR comprises an antigen binding domain, a transmembrane domain, a costimulatory signaling region comprising the CD2 signaling domain, and a CD3 zeta signaling domain, and wherein the antigen binding domain is selected to specifically recognize the target cell population or tissue.

The invention provides a method of providing an anti-tumor immunity in a mammal, the method comprising administering to the mammal an effective amount of a cell genetically modified to express a CAR, wherein the CAR comprises an antigen binding domain, a transmembrane domain, a costimulatory signaling region comprising the CD2 signaling domain, and a CD3 zeta signaling, thereby providing an anti-tumor immunity in the mammal.

The invention provides a method of treating a mammal having a disease, disorder or condition associated with an elevated expression of a tumor antigen, the method comprising administering to the mammal an effective amount of a cell genetically modified to express a CAR, wherein the CAR comprises an antigen binding domain a transmembrane domain, a costimulatory signaling region comprising the CD2 signaling domain, and a CD3 zeta signaling domain, thereby treating the mammal.

In one embodiment, the cell is an autologous T cell.

The invention provides a method of treating a human with cancer, the method comprising administering to the human a T cell genetically engineered to express a CAR, wherein the CAR comprises an antigen binding domain, a transmembrane domain, a costimulatory signaling region comprising the CD2 signaling domain, and a CD3 zeta signaling domain.

In one embodiment, the human is resistant to at least one chemotherapeutic agent.

The invention provides a method of generating a persisting population of genetically engineered T cells in a human diagnosed with cancer, the method comprising administering to the human a T cell genetically engineered to express a CAR, wherein the CAR comprises an antigen binding domain a transmembrane domain, a costimulatory signaling region comprising the CD2 signaling domain, and a CD3 zeta signaling domain, wherein the persisting population of genetically engineered T cells persists in the human for at least one month after administration.

In one embodiment, the persisting population of genetically engineered T cells comprises at least one cell selected from the group consisting of a T cell that was administered to the human, a progeny of a T cell that was administered to the human, and a combination thereof.

In one embodiment, the persisting population of genetically engineered T cells comprises a memory T cell.

In one embodiment, the cancer is chronic lymphocytic leukemia. In one embodiment, the chronic lymphocytic leukemia is refractory CD19+ leukemia and lymphoma.

In one embodiment, the persisting population of genetically engineered T cells persists in the human for at least three months after administration.

In one embodiment, the persisting population of genetically engineered T cells persists in the human for at least four months, five months, six months, seven months, eight months, nine months, ten months, eleven months, twelve months, two years, or three years after administration.

In one embodiment, the cancer is treated.

The invention provides a method of expanding a population of genetically engineered T cells in a human diagnosed with cancer, the method comprising administering to the human a T cell genetically engineered to express a CAR, wherein the CAR comprises an antigen binding domain, a transmembrane domain, a costimulatory signaling region comprising the CD2 signaling domain, and a CD3 zeta signaling domain, wherein the administered genetically engineered T cell produces a population of progeny T cells in the human.

In one embodiment, the progeny T cells in the human comprise a memory T cell.

In one embodiment, the T cell is an autologous T cell.

In one embodiment, the human is resistant to at least one chemotherapeutic agent.

The invention includes a method of modulating the amount of cytokine secreted by a T cell, said method comprising genetically engineering the T cell to express a CAR, wherein the CAR comprises an antigen binding domain, a transmembrane domain, a costimulatory domain region comprising CD2, and a CD3 zeta signaling domain.

In one embodiment, modulating the amount of cytokine secreted by a T cell reduces the proliferation of T regulatory cells.

The invention includes a method of reducing the amount of activation-induced calcium influx into a T cell, said method comprising genetically engineering the T cell to express a CAR, wherein the CAR comprises an antigen binding domain, a transmembrane domain, a costimulatory domain region comprising CD2, and a CD3 zeta signaling domain.

In one embodiment, reducing the amount of activation-induced calcium influx into a T cell prevents the activation-induced cell death of the T cell.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 depicts the nucleotide sequence for the antiCD19-CD2zeta CAR (SEQ ID NO: 1).

FIG. 3 depicts the results of example experiments demonstrating that CD2 CARs release cytokines characteristic of effective immune response. mRNA CAR-electroporated normal human donor T cells were co-cultured for 24 hours with target tumor cells and cytokine secretion was measured. IL-2 and IFN-γ is increased in SS1CD2z, similar to SS128z (top). However, CD2 signal diminishes cytokine secretion in SS128CD2z. CD19CD2z CAR produces similar amounts IL-2 and IFN-g compared to CD19z and CD1928z.

DETAILED DESCRIPTION

Figure 2A:
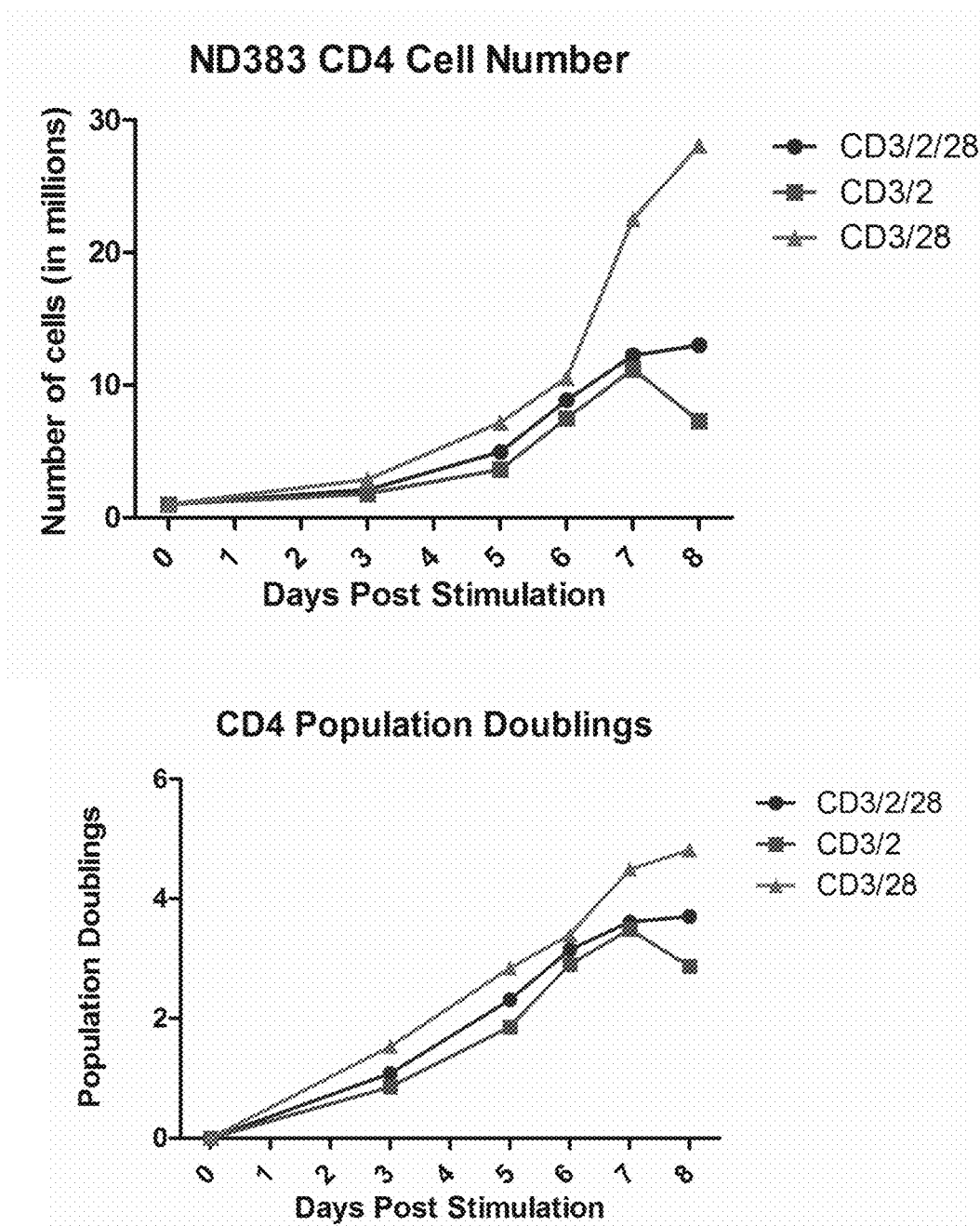
FIGS. 2A-2C are series of graphs depicting the results of example experiments demonstrating that T cells activate and proliferate from CD3/CD2 signals. Normal Human donor CD4 and CD8 T cells were stimulated with magnetic beads coated with αCD2 (T11.1 and T11.2), αCD3 (OKT3), and αCD28 (9.3) antibodies. Absolute cell number and population doublings demonstrate cell proliferation (FIGS. 2A-2C). Cell size represents state of cell activation (FIG. 2B and FIG. 2C). Activation by CD2/CD3 signals sufficiently induces cell activation and proliferation.

The invention relates to compositions and methods for treating cancer, including, but not limited to hematologic malignancies and solid tumors. The present invention relates to a strategy of adoptive cell transfer of T cells modified to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity.

The present invention provides for the incorporation of CD2 into a CAR in order to alter the cytokine production of T cells that are engineered to express the CAR comprising CD2. As discussed elsewhere herein, CD2 can be incorporated into a CAR to both negatively and positively regulate cytokine production of T cells. Therefore, the use of CD2 in a CAR can alter CAR T cell survival and activation induced cell death thresholds.

In one embodiment, the invention provides a method of modulating the amount of cytokine secreted by a T cell. The method comprises genetically engineering the T cell to express a CAR wherein the CAR comprises an antigen binding domain, a transmembrane domain, a costimulatory domain region comprising CD2, and a CD3 zeta signaling domain.

In another embodiment, the invention provides a method of reducing the amount of activation-induced calcium influx into a T cell. The method comprises genetically engineering the T cell to express a CAR, wherein the CAR comprises an antigen binding domain, a transmembrane domain, a costimulatory domain region comprising CD2, and a CD3 zeta signaling domain.

The present invention relates generally to the use of T cells genetically modified to stably express a desired CAR. T cells expressing a CAR are referred to herein as CAR T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular domain of the CD3-zeta chain or FcγRI protein into a single chimeric protein.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. Preferably, the transmembrane domain is the CD8α hinge domain.

With respect to the cytoplasmic domain, the CAR of the invention can be designed to comprise the CD2, CD28 and/or 4-1BB signaling domain by itself or be combined with any other desired cytoplasmic domain(s) useful in the context of the CAR of the invention. In one embodiment, the cytoplasmic domain of the CAR can be designed to further comprise the signaling domain of CD3-zeta. For example, the cytoplasmic domain of the CAR can include, but is not limited to, CD3-zeta, CD2, 4-1BB and CD28 signaling modules, and combinations thereof. Accordingly, the invention provides CAR T cells and methods of their use for adoptive therapy.

In one embodiment, the CAR T cells of the invention can be generated by introducing a lentiviral vector comprising the desired CAR, for example a CAR comprising anti-CD19, CD8α hinge and transmembrane domain, and human CD2 and CD3zeta signaling domains, into the cells. In one embodiment, the CART cells of the invention are able to replicate in vivo resulting in long-term persistence that can lead to sustained tumor control.

In another embodiment, the CAR T cells of the invention can be generated by transfecting an RNA encoding the desired CAR, for example a CAR comprising anti-CD19, CD8α hinge and transmembrane domain, and human CD2 and CD3-zeta signaling domains, into the cells. In one embodiment, the CAR is transiently expressed in the genetically modified CAR T cells.

In one embodiment the invention relates to administering a genetically modified T cell expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

In one embodiment, the invention relates to genetically modified T cells expressing a CAR for the treatment of a patient with cancer. The present invention is based upon the finding that the inclusion of the CD2 signaling domain within the cytoplasmic domain of a CAR significantly influences cytokine production and calcium signaling in CAR modified T cells. In one embodiment, inclusion of the CD2 signaling domain increases cytokine production. In another embodiment, inclusion of the CD2 signaling domain reduces cytokine production. Therefore, the CD2 signaling domain within the cytoplasmic domain of a CAR, either alone or in combination with other cytoplasmic signaling domains, positively and negatively regulates cytokine production at the tumor site. In another embodiment, the CD2 signaling domain within a CAR reduces calcium influx, thereby preventing activation-induced cell death of the genetically modified CAR.

In yet another embodiment, the invention relates generally to the treatment of a patient at risk of developing cancer. The invention also includes treating a malignancy or an autoimmune disease in which chemotherapy and/or immunotherapy in a patient results in significant immunosuppression in the patient, thereby increasing the risk of the patient of developing cancer.

The invention includes using T cells expressing an anti-CD19 CAR, including both CD3-zeta and the CD2 costimulatory domain (also referred to as CART19 T cells). In one embodiment, the CART19 T cells of the invention can undergo robust in vivo T cell expansion and can establish CD19-specific memory cells that persist at high levels for an extended amount of time in blood and bone marrow. In some instances, the CART19 T cells of the invention infused into a patient can eliminate leukemia cells in vivo in patients with advanced chemotherapy-resistant CLL. However, the invention is not limited to CART19 T cells. Rather, the invention includes any antigen binding domain (e.g. anti-mesothelin) fused with one or more intracellular domains selected from the group of a CD2 signaling domain, a CD137 (4-1BB) signaling domain, a CD28 signaling domain, a CD3zeta signal domain, and any combination thereof.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for treating cancer, as well as other diseases. The cancer may be a hematological malignancy, a solid tumor, a primary or a metastasizing tumor. Other diseases treatable using the compositions and methods of the invention include viral, bacterial and parasitic infections as well as autoimmune diseases.

In one embodiment, the invention provides a cell (e.g., T cell) engineered to express a CAR, wherein the CAR T cell exhibits an antitumor property. The CAR of the invention can be engineered to comprise an extracellular domain having an antigen binding domain fused to an intracellular signaling domain of the T cell antigen receptor complex zeta chain (e.g., CD3-zeta). The CAR of the invention when expressed in a T cell is able to redirect antigen recognition based on the antigen binding specificity. An exemplary antigen is CD19 because this antigen is expressed on malignant B cells. However, the invention is not limited to targeting CD 19. Rather, the invention includes any antigen binding domain that when bound to its cognate antigen, affects a tumor cell so that the tumor cell fails to grow, is prompted to die, or otherwise is affected so that the tumor burden in a patient is diminished or eliminated. The antigen binding domain is preferably fused with an intracellular domain from one or more of a costimulatory molecule and a zeta chain. Preferably, the antigen binding domain is fused with one or more intracellular domains selected from the group of a CD2 signaling domain, CD137 (4-1BB) signaling domain, a CD28 signaling domain, a CD3zeta signal domain, and any combination thereof.

In one embodiment, the CAR of the invention comprises a CD2 signaling domain. This is because the present invention is partly based on the discovery that CAR-mediated T-cell responses can be further enhanced with the addition of costimulatory domains. For example, inclusion of the CD2 signaling domain significantly influenced cytokine production in both positive and negative directions, dependent on the presence and identity of other costimulatory domains in the expressed CAR. In one embodiment, the invention comprises a CAR comprising both CD2 and CD28 domains. In one embodiment, a modified T cell expressing a CAR with both the CD2 and CD28 domains releases significantly less IL-2 compared to T cells expressing a CAR with CD28 but not CD2. In one embodiment, a modified T cell that releases less IL-2 reduces the proliferation of immunosuppressive Treg cells. Further, inclusion of the CD2 signaling domain significantly reduced calcium influx. In one embodiment, the reduction of calcium influx by inclusion of CD2 reduces activation induced CAR T cell death.

In some embodiments, the present invention is directed to a retroviral or lentiviral vector encoding a CAR that is stably integrated into a T cell and stably expressed therein. In other embodiments, the present invention is directed to an RNA encoding CAR that is transfected into a T cell and transiently expressed therein. Transient, non-integrating expression of CAR in a cell mitigates concerns associated with permanent and integrated expression of CAR in a cell.

Compositions

The present invention provides a chimeric antigen receptor (CAR) comprising an extracellular and intracellular domain. The extracellular domain comprises a target-specific binding element otherwise referred to as an antigen binding domain. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The present invention includes retroviral and lentiviral vector constructs expressing a CAR that can be directly transduced into a cell. The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the CAR.

Preferably, the CAR comprises an extracellular domain, a transmembrane domain and a cytoplasmic domain. The extracellular domain and transmembrane domain can be derived from any desired source of such domains.

Antigen Binding Domain

The extracellular domain may be obtained from any of the wide variety of extracellular domains or secreted proteins associated with ligand binding and/or signal transduction. In one embodiment, the extracellular domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

The extracellular domain can be directed to any desired antigen. For example, when an antitumor CAR is desired, the extracellular domain chosen to be incorporated into the CAR can be an antigen that is associated with the tumor. The tumor may be any type of tumor as long as it has a cell surface antigen which is recognized by the CAR. In another embodiment, the CAR may one for which a specific monoclonal antibody currently exists or can be generated in the future.

In one embodiment, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the retroviral or lentiviral vector comprising comprises a CAR designed to be directed to an antigen of interest by way of engineering a desired antigen into the CAR. In the context of the present invention, "tumor antigen" or "hyperporoliferative disorder antigen" or "antigen associated with a hyperproliferative disorder" refer to antigens that are common to specific hyperproliferative disorders. In certain aspects, the hyperproliferative disorder antigens of the present invention are derived from cancers including, but not limited to, primary or metastatic melanoma, mesothelioma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

In another embodiment, the template for the RNA CAR is designed to be directed to an antigen of interest by way of engineering a desired antigen binding domain into the CAR. In the context of the present invention, "tumor antigen" or "hyperporoliferative disorder antigen" or "antigen associated with a hyperproliferative disorder" refer to antigens that are common to specific hyperproliferative disorders. In certain aspects, the hyperproliferative disorder antigens of the present invention are derived from cancers including, but not limited to, primary or metastatic melanoma, mesothelioma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

Tumor antigens are proteins that are produced by tumor cells that elicit an immune response, particularly T-cell mediated immune responses. In one embodiment, the tumor antigen of the present invention comprises one or more antigenic cancer epitopes immunologically recognized by tumor infiltrating lymphocytes (TIL) derived from a cancer tumor of a mammal. The selection of the antigen binding domain of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding domain portion of the CAR targets an antigen that includes but is not limited to CD19, CD20, CD22, ROR1, Mesothelin, CD33/IL3Ra, c-Met, PSMA, Glycolipid F77, EGFRvIII, GD-2, MY-ESO-1 TCR, MAGE A3 TCR, and the like.

Depending on the desired antigen to be targeted, the CAR of the invention can be engineered to include the appropriate antigen bind moiety that is specific to the desired antigen target. For example, if CD19 is the desired antigen that is to be targeted, an antibody for CD19 can be used as the antigen bind moiety for incorporation into the CAR of the invention.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD2 as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of CD2. In yet another embodiment, the cytoplasmic domain is designed to comprise the signaling domain of CD3-zeta and the signaling domain of CD28 and CD2. In yet another embodiment, the cytoplasmic domain is designed to comprise the signaling domain of CD3-zeta and the signaling domain of CD28, CD2, and 4-1BB.

Vectors

The present invention encompasses a DNA construct comprising the sequence of a CAR, wherein the sequence comprises the nucleic acid sequence of an antigen binding domain operably linked to the nucleic acid sequence of an intracellular domain. An exemplary intracellular domain that can be used in the CAR of the invention includes but is not limited to the intracellular domain of CD3-zeta, CD28, 4-1BB, CD2 and the like. In some instances, the CAR can comprise any combination of CD3-zeta, CD28, 4-1BB, CD2 and the like.

In one embodiment, the CAR of the invention comprises anti-CD19 scFv, human CD8 hinge and transmembrane domain, and human CD2 and CD3zeta signaling domains. In one embodiment, the CAR of the invention comprises the nucleic acid sequence set forth in SEQ ID NO: 1. In another embodiment, the CAR of the invention comprises the amino acid sequence encoded by the nucleic acid set forth in SEQ ID NO: 1.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In one embodiment, the genetically modified T cells of the invention are modified through the introduction of RNA. In one embodiment, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention. For example, the template for the RNA CAR comprises an extracellular domain comprising a single chain variable domain of an anti-tumor antibody; a transmembrane domain comprising the hinge and transmembrane domain of CD8α; and a cytoplasmic domain comprises the signaling domain of CD3-zeta and the signaling domain of CD2

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, t is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun, 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified T Cells

In some embodiments, the CAR sequences are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the Med-Pulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD 14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol. Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) modified to express a CAR that combines an antigen recognition domain of a specific antibody with an intracellular domain of CD3-zeta, CD28, 4-1BB, CD2, or any combinations thereof. Therefore, in some instances, the modified T cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3zeta, and a costimulatory signaling region.

In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, CAR T cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding domain in the CAR. For example, a CART19 cells elicits an immune response specific against cells expressing CD19.

While the data disclosed herein specifically disclose mRNA comprising either anti-CD19 scFv derived from FMC63 murine monoclonal antibody or the anti-mesothelin SS1 scFv, along with human CD8α hinge and transmembrane domain, and human CD2 and CD3zeta signaling domains, the invention should be construed to include any number of variations for each of the components of the construct as described elsewhere herein. That is, the invention includes the use of any antigen binding domain in the CAR to generate a CAR-mediated T-cell response specific to the antigen binding domain. For example, the antigen binding domain in the CAR of the invention can target a tumor antigen for the purposes of treat cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen bind moiety portion of the CAR of the invention is designed to treat a particular cancer. For example, the CAR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In another embodiment, the CAR can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, the CAR can be designed to target mesothelin to treat mesothelioma, pancreatic cancer, ovarian cancer, and the like. In another embodiment, the CAR can be designed to target CD33/IL3Ra to treat acute myelogenous leukemia and the like. In a further embodiment, the CAR can be designed to target c-Met to treat triple negative breast cancer, non-small cell lung cancer, and the like.

In one embodiment, the CAR can be designed to target PSMA to treat prostate cancer and the like. In another embodiment, the CAR can be designed to target Glycolipid F77 to treat prostate cancer and the like. In a further embodiment, the CAR can be designed to target EGFRvIII to treat glioblastoma and the like.

In one embodiment, the CAR can be designed to target GD-2 to treat neuroblastoma, melanoma, and the like. In another embodiment, the CAR can be designed to target NY-ESO-1 TCR to treat myeloma, sarcoma, melanoma, and the like. In a further embodiment, the CAR can be designed to target MAGE A3 TCR to treat myeloma, sarcoma, melanoma, and the like.

However, the invention should not be construed to be limited to solely to the antigen targets and diseases disclosed herein. Rather, the invention should be construed to include any antigenic target that is associated with a disease where a CAR can be used to treat the disease.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an antitumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Use of the CD2 Signaling Domain in Second-Generation Chimeric Antigen Receptors

The incorporation of costimulatory domains into chimeric antigen receptors can increases cytokine production and target cell killing. CD2 is a costimulatory molecule that may influence calcium-mediated signaling. It is herein examined whether inclusion of the CD2 intracellular domain into CARs influences calcium influx/signaling and cytokine production.

The materials and methods employed in these experiments are now described.

CD2-Containing CARs

The CD2 costimulatory domain was cloned into various CD19 or mesothelin specific CARs. For example, FIG. 1 displays the nucleotide sequence for the antiCD19-CD2z CAR (SEQ ID NO: 1).

T Cells

Blood samples were obtained from the Human Immunology Core of the University of Pennsylvania. Peripheral blood $CD4^+$ and $CD8^+$ T cells were negatively isolated using RosetteSep Kits (Stem cell Technologies). Cells were cultured in RPMI 1640 media supplemented with 10% FCS, 100-U/ml penicillin, 100 µg/ml streptomycin sulfate, 10 mM Hepes in a 37° C. and 5% $CO_2$ incubator. For stimulation, $CD4^+$ and $CD8^+$ T cells were cultured with a combination of αCD2(T11.1 and T11.2), αCD3 (OKT3), and/or αCD28 (9.3) antibody coated magnetic beads.

mRNA Electroporation

Human T cells were electroporated with mRNA to express the CD28:CD3zeta domain, CD28:CD2:CD3zeta or the CD2:CD3zeta domains. In addition, CARs were prepared to express only the CD2, CD28 or CD3zeta domains. Donor T cells were electroporated with CAR mRNA by the following methods. On day 10 of culture, the magnetic bead activated T cells were collected and electroporated. Two electroporation systems were used: BTX CM830 (Harvard Apparatus BTX, Holliston, Mass., USA), and Maxcyte (Maxcyte Inc, Rockville, Md., USA). For electroporation using BTX EM830, the stimulated T cells subjected to electroporation were washed three times with OPTI-MEM (Invitrogen) and resuspended in OPTI-MEM at the final concentration of $1-3\times10^8$/ml. Subsequently, 0.1 to 0.2 ml of the cells was mixed with 10 µg/0.1 ml T cells of IVT RNA (or as indicated) and electroporated in a 2-mm cuvette (Harvard Apparatus BTX, Holliston, Mass., USA). For electroporation using Maxcyte, the instruction manual was followed using OC-400 processing chamber (Maxcyte Inc, Rockville, Md., USA) with integrated programs. Expression of the CARs was verified by flow cytometry. Cells were washed and suspended in FACs buffer (PBS plus 0.1% sodium azide and 0.4% BSA). Biotin-labeled polyclonal goat anti-mouse F(ab)2 antibodies (anti-Fab, Jackson Immunoresearch, West Grove, Pa.) were added to the tube and the cells were incubated at 4° C. for 25 minutes and washed twice. The cells were then stained with phycoerythrin-labeled streptavidin (BD Pharmingen, San Diego, Calif.).

Cytokine Secretion

K562 target cells expressing mesothelin or CD19 were washed and suspended at $10^6$ cells/mL in R10. One hundred thousand of each target cell type were added to each of 2 wells of a 96 well round bottom plate (Corning). Effector CAR T cell cultures were washed and suspended at $10^6$ cells/mL in R10. One hundred thousand effector T cells were combined with target cells in the indicated wells of the 96 well plate. In addition, wells containing T cells alone were prepared. The plates were incubated at 37° C. for 18 to 20 hours. After the incubation, supernatant was harvested and subjected to an ELISA assay for IL-2 and IFN-gamma using standard methods (Pierce, Rockford, Ill.).

Specific Target Lysis mRNA electroporated CAR T cells were co-cultured with various cancer cell lines and analyzed by flow cytometry for specific target lysis.

Measuring Calcium Influx mRNA electroporated CAR T cells were loaded with indo-1 and stimulated with mesothelin-Fc fusion protein. Calcium influx in cells was measured post stimulation by observing the ratio of bound to free calcium.

The results of the experiments are now described.

Results

Figure 2B:
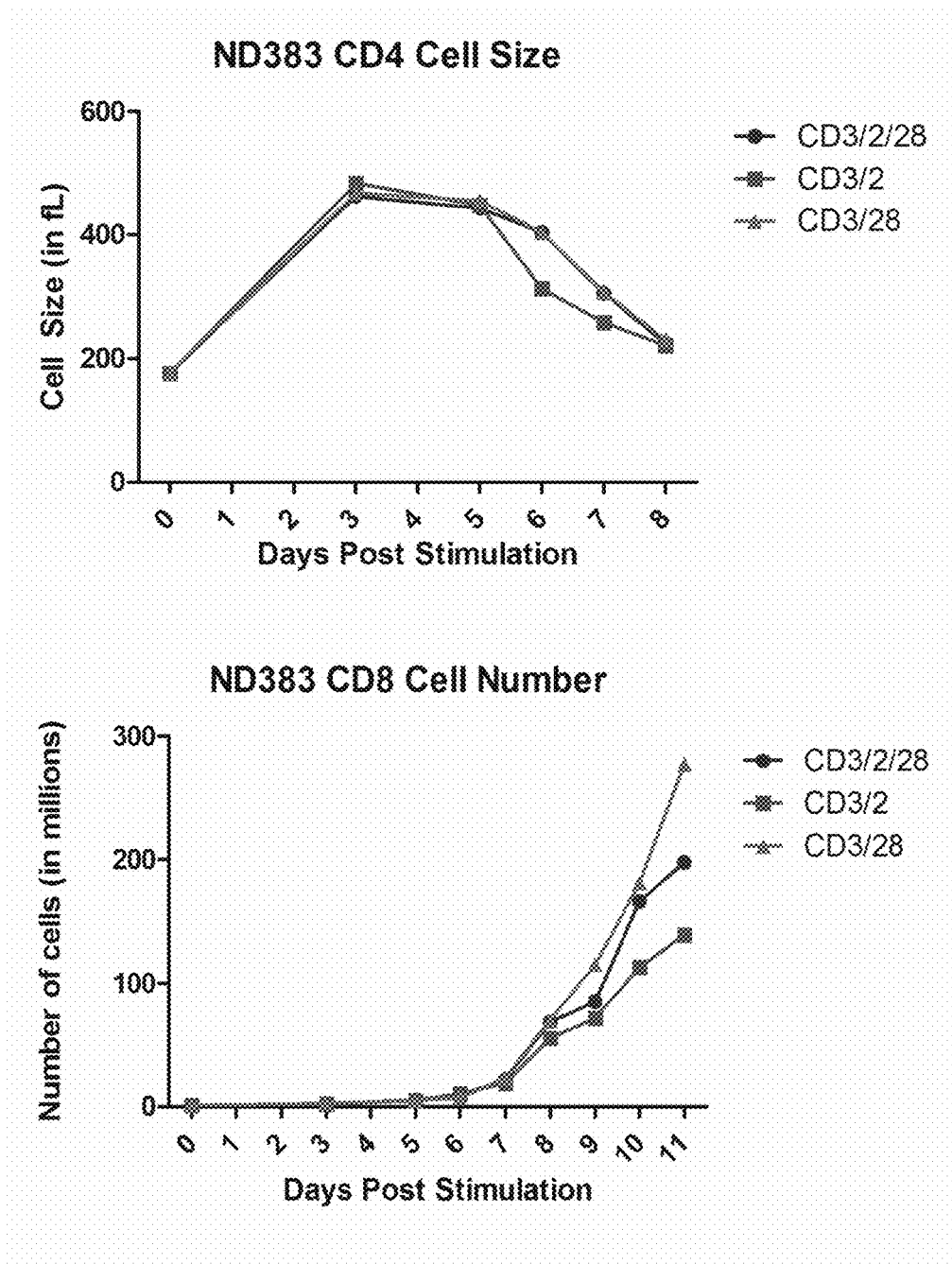
Figure 2C:
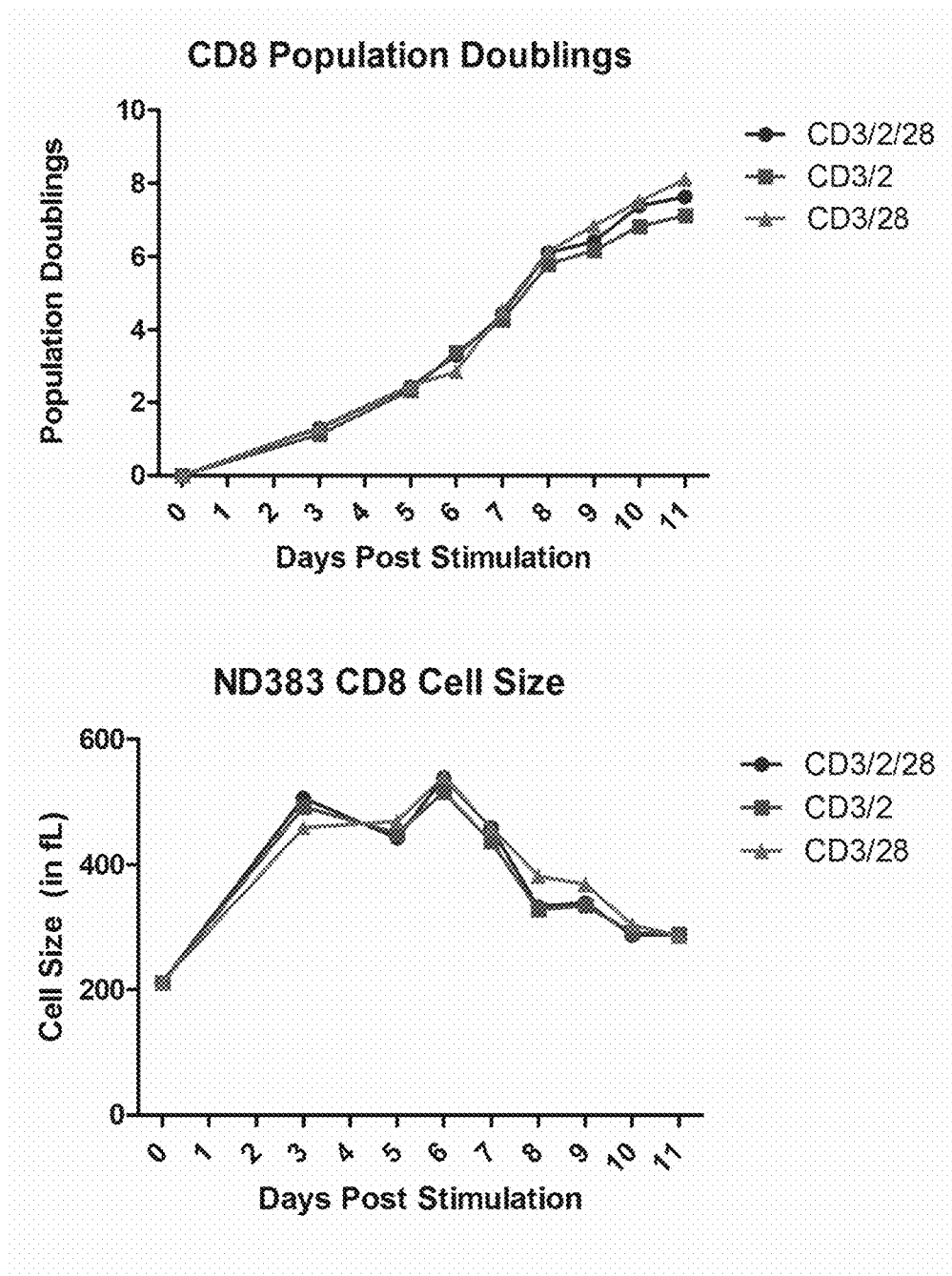

Normal human donor CD4 and CD8 T cells were obtained and stimulated with a combination of αCD2 (T11.1 and T11.2), αCD3 (OKT3), and/or αCD28 (9.3) antibody coated magnetic beads. After stimulation, cell proliferation was assessed by observing the absolute cell number and population doublings, while cell activation was assessed by measuring cell size. Activation by CD2/CD3 signals sufficiently induces cell activation and cell proliferation of both CD4 and CD8 T cell populations (FIGS. 2A-2C).

Human T cells were electroporated with mRNA for various CAR constructs, either containing or not containing the CD2 signaling domain. The mRNA electroporated T cells were co-cultured for 24 hours with target tumor cells after which cytokine secretion was measured. IL-2 and IFN-γ secretion is increased in SS1-CD2z, similar to what is observed in SS1-28z. However, IL-2 and IFN-γ secretion is diminished in SS1-28CD2z. Similarly, anti-CD19-CD2z produces similar IL-2 and IFN-γ compared to anti-CD19-z and anti-CD19-28z, but IL-2 and IFN-γ secretion is diminished in anti-CD19-28CD2z CARs (FIG. 3). The observation that CD2 signaling domains allow CAR T cells to proliferate while diminishing cytokine secretion may be important in some therapeutic instances. For instance, in one case a patient with leukemia treated with a CD19 CAR containing a CD28 signaling domain succumbed due to high levels of cytokines (Brentjens et al, 2010, Mol Ther, 8(4): 666-8). Similarly, a patient with colon cancer died shortly after being injected with her2/neu CAR T cells that contained a CD28 signaling domain (Morgan et al, 2010, Mol Ther, 18(4):843-51).

Figure 4:
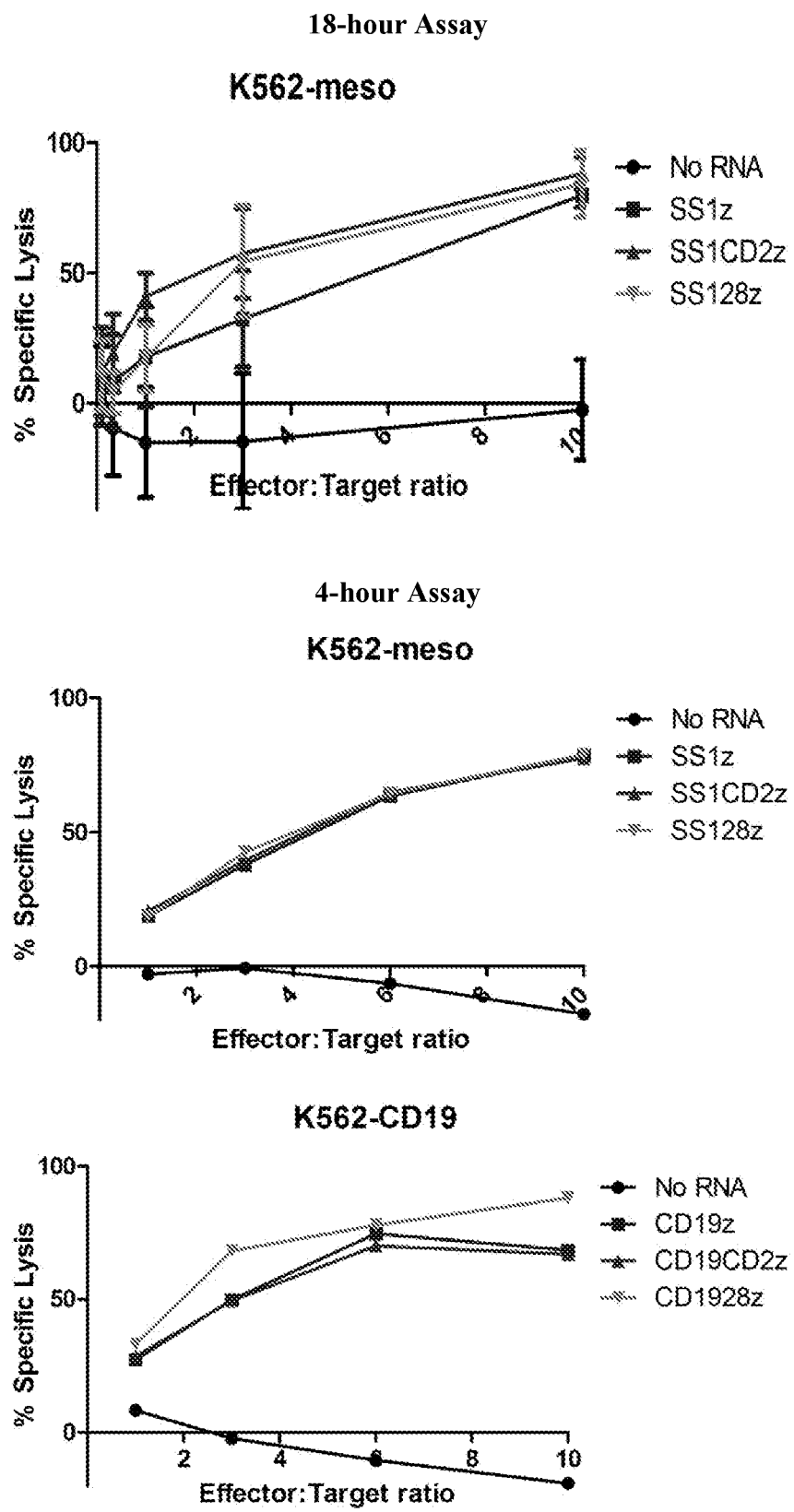
FIG. 4 depicts the results of example experiments demonstrating that CARs with the CD2 signaling domain are effective at killing tumor cells. mRNA CAR-electroporated normal human donor T cells were co-cultured with target tumor cells for 18 hours (left) and 4 hours (right) at varying effector:target ratios. CD2 CARs efficiently eliminate tumor cells in both assays, comparable CARs with CD3z or CD28z signaling domains.

To assess the tumor killing ability of CD2-containing CARs, mRNA electroporated T cells were co-cultured with target tumor cells at varying effector to target ratios. After 4 hours of co-culture, anti-CD 19-CD2z CARs efficiently eliminated K562-CD19 tumor cells, while SS1-CD2z CARs efficiently eliminated K562-meso tumor cells. Further, after 18 hours of co-culture, SS1-CD2z displayed effective killing of K562-meso tumor cells (FIG. 4).

Figure 5:
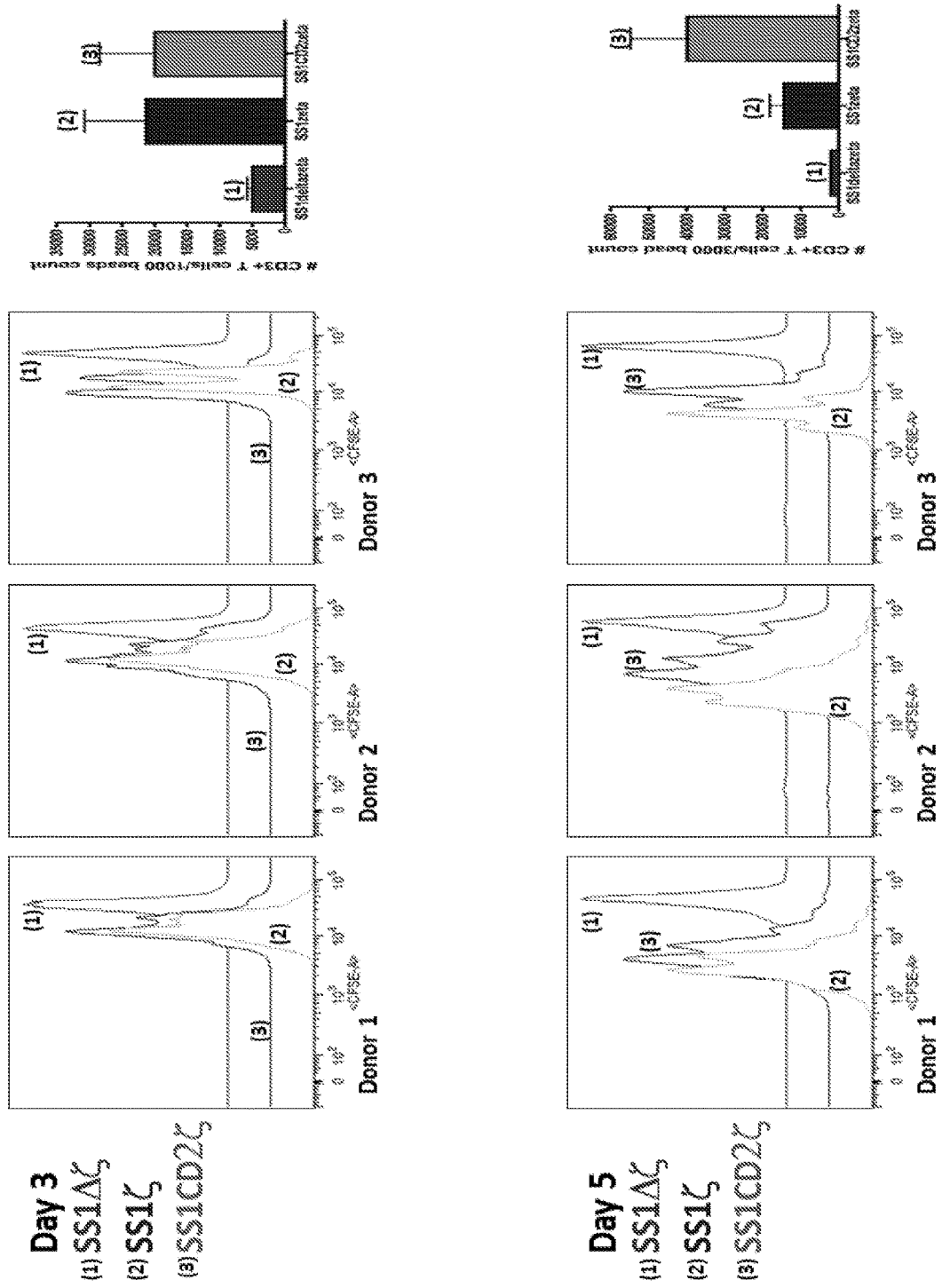
FIG. 5 depicts the results of an example experiment demonstrating that CD2 signaling domain improves T-cell proliferation when CAR-electroporated normal human donor T cells were co-cultured with target tumor cells for 5 days. There is no significant difference in the number of CD2 CAR-T cells at 3 days of stimulation, but there is a two-fold increase in the number of CD2 CAR-T cells after 5 days, suggesting that CD2 signaling domain contributes to increased T-cell proliferation when added to a CAR.

To evaluated calcium signals, mRNA CAR electroporated T cells were loaded with Indo-1AM calcium indicator and stimulated with mesothelin-Fc fusion protein (30 seconds after recording). The ratio of bound to free calcium was recorded over time. Inclusion of the CD2 signaling domain squelches calcium flux, as can be seen by the reduction in calcium influx in SS1-28CD2z compared to SS1-28z (without CD2) (FIG. 5). While not wishing to be held to any particular theory, the observation that CD2 signaling diminishes the calcium flux is likely causally related to the diminished cytokine secretion. This may be important in some therapeutic instances. For instance, in one case a patient with leukemia treated with a CD19 CAR containing a CD28 signaling domain succumbed due to high levels of cytokines (Brentjens et al, 2010, Mol Ther, 8(4):666-8). Similarly, a patient with colon cancer died shortly after being injected with her2/neu CAR T cells that contained a CD28 signaling domain (Morgan et al, 2010, Mol Ther, 18(4):843-51).

Figure 6:
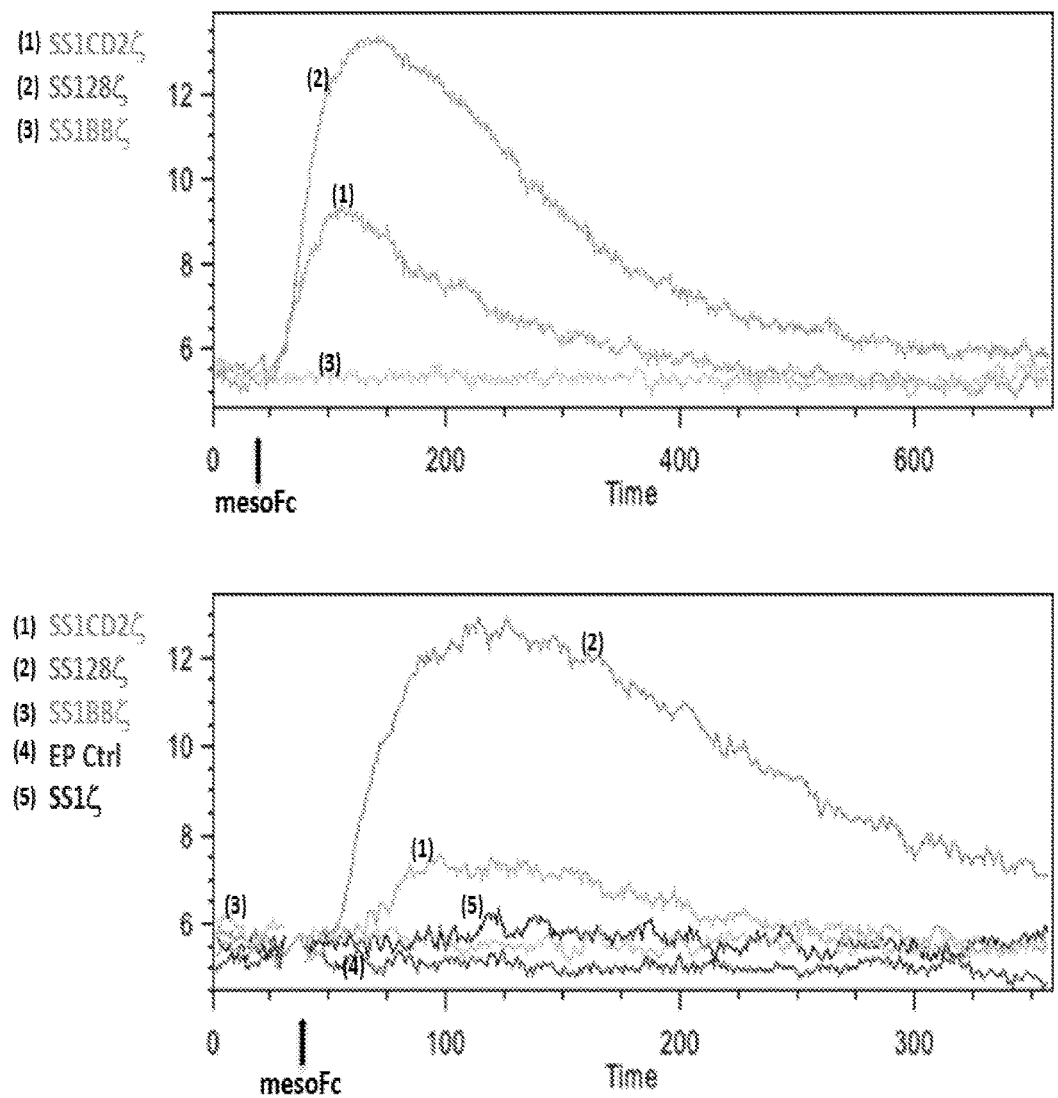
FIG. 6 depicts the results of an example experiment demonstrating the calcium flux response of CAR-T cells with the CD28, CD2, CD137 signaling domains in addition to the CD3zeta domain. mRNA CAR-electroporated normal human donor T cells were loaded with Indo-1 AM calcium indicator and stimulated with mesothelin-Fc fusion protein 30 seconds after the start of recording. Shown are the ratios of bound calcium (Indo-1 violet) to free calcium (Indo-1 blue) over time. Additions of the CD2 signaling domain to SS1z increases the calcium flux signal, but not as strong as the SS128z calcium flux.

The results presented herein show that CD2z CARs induce cytokine production on par with 28z CARs, demonstrate a proliferation advantage over first generation CARs (z-alone), and exhibit a calcium flux response intermediate between what was observed for 28z and BBz (FIG. 6).

It is herein reported that use of the CD2 signaling domain in second-generation CARs influences IL-2 and IFN-γ production of CAR-T cells and exhibits similar target cell lysis. These results demonstrate that CD2 can be used in second-generation CAR molecules to alter the cytokine production of CAR-T cells in both negative and positive directions and may have implications for sustainability and effectiveness of CAR-T cells in tumor microenvironments in vivo by altering CAR T cell survival and activation induced cell death thresholds. Given the high self-activation of the SS-128z CAR, SS1-CD2z may be a more tolerable CAR for in vivo mesothelin tumor attack and may decrease activation induced cell death.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid sequence encoding a chimeric antigen receptor (CAR), wherein the CAR comprises an antigen binding domain, a transmembrane domain, a costimulatory signaling region, and a CD3 zeta signaling domain, wherein the costimulatory signaling region comprises the CD2 signaling domain and further wherein the isolated nucleic acid sequence comprises the nucleic acid sequence of SEQ ID NO: 1.

2. A vector comprising a nucleic acid sequence encoding a chimeric antigen receptor (CAR), wherein the CAR comprises an antigen binding domain, a transmembrane domain, a costimulatory signaling region, and a CD3 zeta signaling domain, wherein the costimulatory signaling region comprises the CD2 signaling domain and further wherein the isolated nucleic acid sequence encoding the CAR comprises the nucleic acid sequence of SEQ ID NO: 1.

* * * * *

UNITED STATES PATENT AND TRADEMARK OFFICE
CERTIFICATE OF CORRECTION

Page 1 of 1

PATENT NO. : 9,783,591 B2
APPLICATION NO. : 14/375999
DATED : October 10, 2017
INVENTOR(S) : Carl H. June et al.

It is certified that error appears in the above-identified patent and that said Letters Patent is hereby corrected as shown below:

In the Specification

On Column 1, Lines 16-21, please replace the existing paragraph with the following paragraph:
-- STATEMENT REGARDING FEDERALLY SPONSORED RESEARCH OR DEVELOPMENT
This invention was made with government support under grant number CA120409 awarded by the National Institutes of Health. The government has certain rights in the invention. --

Signed and Sealed this
Twelfth Day of February, 2019

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 1691
<212> TYPE: DNA
<213> ORGANISM: Artificial Sequence
<220> FEATURE:
<223> OTHER INFORMATION: Chemically Synthesized

<400> SEQUENCE: 1
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
gggggcacca agctggagat cacaggtggc ggtggctcgg gcggtggtgg gtcgggtggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaagggg tctggagtgg ctgggagtaa tatgggtag tgaaaccaca     600 tactataatt cagctctcaa atccagactg accatcatca aggacaactc caagagccaa     660
gttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcac cacgacgcca gcgccgcgac caccaacacc ggcgcccacc atcgcgtcgc     840
ggcccctgtc cctgcgccca gaggcgtgcc ggccagcggc gggggcgca gtgcacacga     900 gggggctgga cttcgcctgt gatatctaca tctgggcgcc cttggccggg acttgtgggg     960
tccttctcct gtcactggtt atcaccctt actgcaccaa aaggaaaaaa cagaggagtc    1020
ggagaaatga tgaggagctg gagacaagag cccacagagt agctactgaa gaaaggggcc    1080
ggaagcccca ccaaattcca gcttcaaccc ctcagaatcc agcaacttcc caacatcctc    1140
ctccaccacc tggtcatcgt tcccaggcac ctagtcatcg tcccccgcct cctggacacc    1200
gtgttcagca ccagcctcag aagaggcctc ctgctccgtc gggcacacaa gttcaccagc    1260
agaaaggccc gcccctcccc agacctcgag ttcagccaaa acctccccat ggggcagcag    1320
aaaactcatt gtccccttcc tctaatatcg atagagtgaa gttcagcagg agcgcagacg    1380 ccccccgcgta ccagcagggc cagaaccagc tctataacga gctcaatcta ggacgaagag    1440
aggagtacga tgttttggac aagagacgtg gccgggaccc tgagatgggg ggaaagccga    1500
gaaggaagaa ccctcaggaa ggcctgtaca atgaactgca gaaagataag atggcggagg    1560
```

```
cctacagtga gattgggatg aaaggcgagc gccggagggg caagggcac gatggcctt    1620 accagggtct cagtacagcc accaaggaca cctacgacgc ccttcacatg caggccctgc    1680
cccctcgcta a                                                         1691
```